United States Patent [19]
Kearney et al.

[11] Patent Number: 5,354,460
[45] Date of Patent: Oct. 11, 1994

[54] FLUID TRANSFER SYSTEM WITH UNIFORM FLUID DISTRIBUTOR

[75] Inventors: Michael M. Kearney; Kenneth R. Petersen, both of Twin Falls; Teunis Vervloet, Nampa; Michael W. Mumm, Kimberly, all of Id.

[73] Assignee: The Amalgamated Sugar Company, Ogden, Utah

[21] Appl. No.: 10,606

[22] Filed: Jan. 28, 1993

[51] Int. Cl.⁵ .............................................. B01D 15/08
[52] U.S. Cl. .................... 210/198.2; 210/289; 210/291; 210/456; 210/656; 96/105
[58] Field of Search .............. 210/656, 198.2, 289, 210/291, 456; 55/67, 386; 95/82, 85; 96/101, 105, 107

[56] References Cited
U.S. PATENT DOCUMENTS

| | | | |
|---|---|---|---|
| 2,407,228 | 9/1946 | Forsyth | 210/289 |
| 2,802,573 | 8/1957 | Weatherly | 210/289 |
| 3,230,167 | 1/1966 | Golay | 210/198.2 |
| 3,356,220 | 12/1967 | Zievers | 210/289 |
| 3,789,989 | 2/1974 | Carson | 210/291 |
| 4,354,932 | 10/1982 | McNeil | 210/198.2 |
| 4,469,597 | 9/1984 | Mott | 210/198.2 |
| 4,537,217 | 8/1985 | Allen | 137/561 A |
| 4,582,608 | 4/1986 | Ritacco | 210/198.2 |
| 4,627,918 | 12/1986 | Saxena | 210/198.2 |
| 4,636,315 | 1/1987 | Allen | 210/656 |
| 4,891,133 | 1/1990 | Colvin | 210/456 |
| 4,894,152 | 1/1990 | Colvin | 210/198.2 |
| 4,999,102 | 3/1991 | Cox | 210/137 |
| 5,141,635 | 8/1992 | Le Plang | 210/198.2 |

*Primary Examiner*—Ernest G. Therkorn
*Attorney, Agent, or Firm*—Trask, Britt & Rossa

[57] ABSTRACT

A step-down nozzle for the even distribution of fluids at the interface between phases in a column or cell accommodating a plug flow operation is structured with an internal flow channel of recursive configuration.

7 Claims, 3 Drawing Sheets

FLUID TRANSFER SYSTEM WITH UNIFORM FLUID DISTRIBUTOR

BACKGROUND OF THE INVENTION

1. Field

This invention relates to uniform fluid transfer devices. It is particularly directed to industrial scale fluid transfer systems. It is used in columns or cells constituting a portion of chromatographic, ion-exchange, absorption, separation or distillation process systems.

2. State of the Art

Performance design criteria have evolved in connection with large scale process systems incorporating fluid transfer systems (those with columns or cells having diameters of two feet or larger) as follows:

(1) An ideal uniform distribution of fluid across the distributor or collector device should be approximated as closely as possible. The term "ideal uniform distribution" is intended to designate that a cross section of a flowing fluid of arbitrarily small thickness is taken normal to the flow direction through a column or cell and is mapped to a second similar cross section such that any point on the second cross section maintains the same relative position and relative velocity with respect to all other surface points observed before the mapping. Further, "ideal uniform distribution" is intended to designate that the cross section does not mix with any adjacent surfaces during the mapping.

2) In some process systems using uniform fluid transfer devices, a transition from turbulent to laminar flow occurs. For example, a fluid passing through a small diameter pipe at high velocity experiences turbulent flow. When such a fluid enters a large diameter cell, its velocity decreases, resulting in laminar flow. In a chromatography process, a laminar flow within a resin-filled cell is desired. The transition from turbulent to laminar flow conditions has often subjected a fluid to mixing conditions immediately upon exiting of the fluid from high flow velocity distributor orifices. Such mixing is considered to be undesirable, but it can be avoided through ideal uniform distribution (3) Distributor layouts are generally difficult to configure so as to obtain an ideal uniform distribution on a circular surface. However, because industrial scale processes typically involve cylindrical vessels, i.e. have a cylindrical wall and circular inlet and outlet ends, a distributor layout must be useful in such vessels for practical application.

(4) The distribution and collection systems should both be conducive to plug flow of fluid through solid phase media, such as is common to chromatographic or ion-exchange applications.

(5) The composition of fluids flowing in some processes alternates between two or more liquid phases. For example, a feed stock and eluate may be present, and often a raffinate or other phase is also present. The distribution and collection systems should maintain a well-defined interface between the various liquid phases flowing through the system. Discrete phases should be kept separate by maintaining plug flow characteristics. "Plug flow" implies that respective liquid interfaces of a phase plug reach, respectively and approximately simultaneously, the inlet of the distributor closest to the source and an outlet remote from that source. The same principle applies to the collection system.

(6) For systems containing a solid phase, e.g., chromatography or ion exchange systems, it is desirable to minimize the void between a distributor (or collector) and the surface of the solid phase, thereby reducing the opportunity for back mixing. Any orifice or nozzle system functioning as a distributor and/or collector should be in contact with, or at least in near proximity to, the surface of the solid medium at all times. Structure associated with these elements should desirably provide a barrier against which the solid medium can be packed.

(7) For purposes of practical industrial application, the design of the distributor used should be easy to scale to any desired size.

Various separator systems using distributor/collector systems are disclosed by U.S. Pat. Nos. 2,985,599; 4,001,133; 4,182,633; 4,412,866 and 4,999,102, the disclosures of which are incorporated by reference for their teachings concerning the operation and control of separator systems generally and for their illustrations of various structures and mechanisms relied upon in the separation art for distributing liquids to an interface or collecting liquids from an interface. U.S. Pat. No. 4,412,866 is generally instructive, and FIG. 2 of that patent discloses representative distributor and collector devices. U.S. Patent No. 4,999,102 also discloses distributor and collector systems suitable for use with other apparatus of separator systems for various processes.

U.S. Pat. Nos. 4,537,217 and 4,636,315 disclose small scale fluid distributors formed from solid bodies, such as tiles, with entry openings on one surface and a plurality of distribution openings on the opposite surface corresponding to each entry opening. The entry openings are connected to the distribution openings by internal channels and bores.

As used herein and in the appended claims: The term "fluid system" is intended to designate the apparatus of any unit operation, including those specially identified by this disclosure, in which liquid is either introduced to or withdrawn from a cell at a zone approximately transverse the direction of flow through the cell. The term "cell" is intended to include the terms "vessel" and "column", as well as any other structure utilized by practitioners of the separation arts, to effect a separation and/or extraction of components from an admixture by bringing the admixture into contact with solid or liquid exchange media. "Cross-sectional zone" (or region) refers to a region within a cell bounded by cross sections of the cell oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Hydraulically identical", as applied to conduits, plenums and the like, means that the elements compared react to pressure differentials in a fluid circuit as though they were structurally identical. "Distributor" (or "distribution system") refers to structure through which fluids are introduced to a cell and "collection" or (collection system") refers to structure used to withdraw fluids from a cell, in each instance from a cross-sectional zone. The term "plenum" is defined in this application as a fluid flow device which receives fluid from a single inlet conduit and discharges the fluid into a plurality of outlet conduits, or receives fluid from a plurality of inlet conduits and discharges it into a single outlet conduit.

SUMMARY OF THE INVENTION

The present invention provides a manifold (header) system which can function as a distributor or a collector in a fluid system. In either application, the manifold system maintains an interface between phases within a large scale cell; that is, a typical cell within a large-scale fluid system. The manifold is of low internal volume as compared to commonly used systems, thereby offering a reduced retention time.

In practice, the manifold system of this invention may be used to introduce fluid (e.g. feed, eluant or system internal flow) to a cell at an inlet zone which occupies or constitutes a cross-sectional region of the cell. Introduction is through a multiplicity of recursive step-down devices, hereinafter designated "step-down nozzles". Fluid is delivered to the step-down nozzles through the manifold system by means of approximately hydraulically identical flow paths comprised of distribution plenums, tubing and ancillary features from a common feed plenum (center well). The step-down nozzles are mounted or suspended within the inlet zone to deliver fluid at a horizontal interface of discrete liquid composition. A multiplicity of such step-down nozzles are arranged in a pattern which assures approximately even distribution of fluid across the entire cell at the interface. A theoretically ideal such pattern positions each passage (or orifice) to supply liquid to an approximately equal area of interface, with appropriate adjustments to take into account the effect of the walls and other internal structure contacted by a fluid plug. Additionally, a theoretically ideal pattern consists of an orifice density providing contiguous flow patterns which completely and uniformly cover the interface surface.

The fluid delivery components of the manifold system include a center well, which is usually, but not necessarily, positioned at the center of the cell. This disclosure assumes, for the sake of simplicity of description, that the cell has a circular horizontal cross section and is oriented approximately vertically; e,g,, as an upstanding column. It is recognized that cells can be fashioned with other cross-sectional configurations, and that in some circumstances plug flow or circulation may be established with substantial horizontal components. This disclosure, being directed to the preferred embodiments, emphasizes the typical cell configuration, with the understanding that the invention can be appropriately modified for incorporation in other configurations.

The center well is hydraulically symmetrical, typically being fashioned as an open cylinder fed by delivery means, such as a launder, pipe, injector or drain. In most instances, feed to the well is at the top, through an adjustable flow. In a typical arrangement, hydraulically equivalent conduit runs (via piping, molded or machined conduits, or similar components) extend from the well at approximately equal spaced radial locations around the circumference of the well. Those skilled in the art are well able to devise various hydraulically equivalent arrangements. Each conduit run (which may constitute a single straight conduit, and that may be called a primary, or primary distribution, conduit) is in open fluid flow communication with the well at a proximal end, and terminates in open fluid flow communication with an intermediate plenum.

The intermediate plenums, which correspond in number to the number of primary conduits, are structured similar to the center well, and serve a similar liquid distribution function; namely to transfer fluid at substantially the same hydraulic characteristics to remote locations.

The manifold system generally includes a convenient number of intermediate stages, with each succeeding stage including a step-down plenum receiving liquid through the terminal end of a conduit in open communication with a larger plenum closer (upstream in the case of a distributor) in the manifold circuit to the center well. In certain instances, intermediate stages may be dispensed with, but when they are present, each step-down stage includes plenums totalling in number the number of conduits extending in open fluid flow communication from the plenums of the next larger (stepped-up) stage. A final, or terminal, stage includes conduits of small internal diameter, i.e. piping, molded or machined conduit, and/or similar components, extending from any of the intermediate stages to terminate in step-down nozzles. The step-down nozzles are configured of conduit patterns using any well known fabrication technique, such as matrices of pipe, molded or machined tiles, or stamped plate. The orifice density of the step-down nozzle can be increased indefinitely by recursively duplicating a basic pattern on smaller and smaller scale. The final density is only restricted by fabrication technique and practical considerations for any particular case.

The distributor has the important characteristic that it can be scaled by simple proportioning of manifold size and by maintaining desired orifice density through adding or removing step-down conduits or orifices on the final nozzle.

BRIEF DESCRIPTION OF THE DRAWINGS

In the drawings, which illustrate what is presently regarded as the best mode for carrying out the invention:

FIGS. 4a, 4b, and 4c are a series of plan views of the structural components of a typical nozzle arrangement, of which FIG. 4a shows a central distributor element, FIG. 4b a nozzle exit plate and FIG. 4c an inlet cover plate.

DESCRIPTION OF THE ILLUSTRATED EMBODIMENTS

Figure 1:
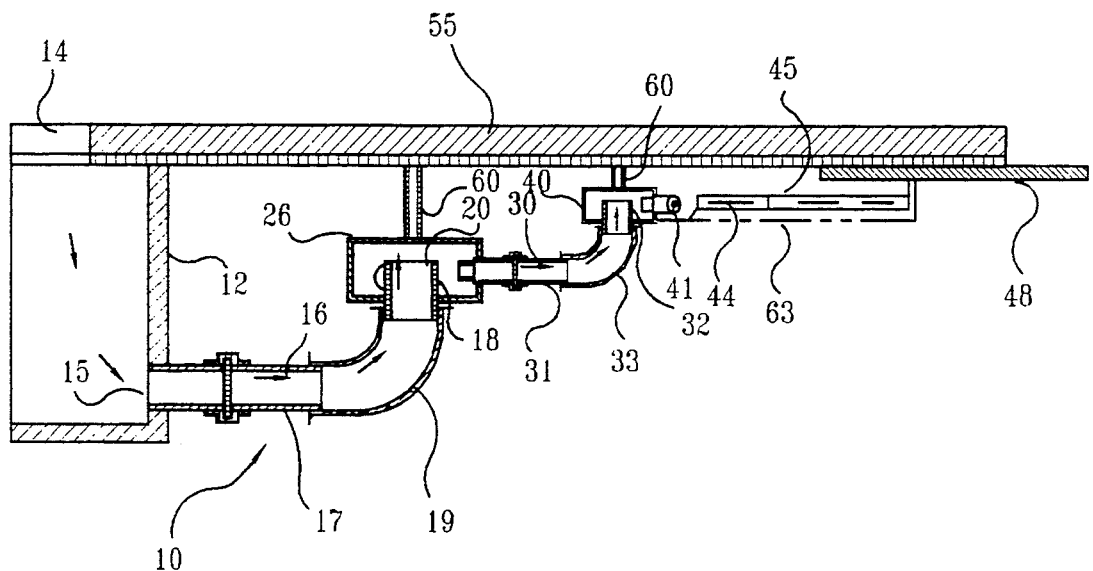
FIG. 1 is a view, in section, of a manifold system of the invention installed as a distributor and using pipe for conduit fabrication.
Figure 2:
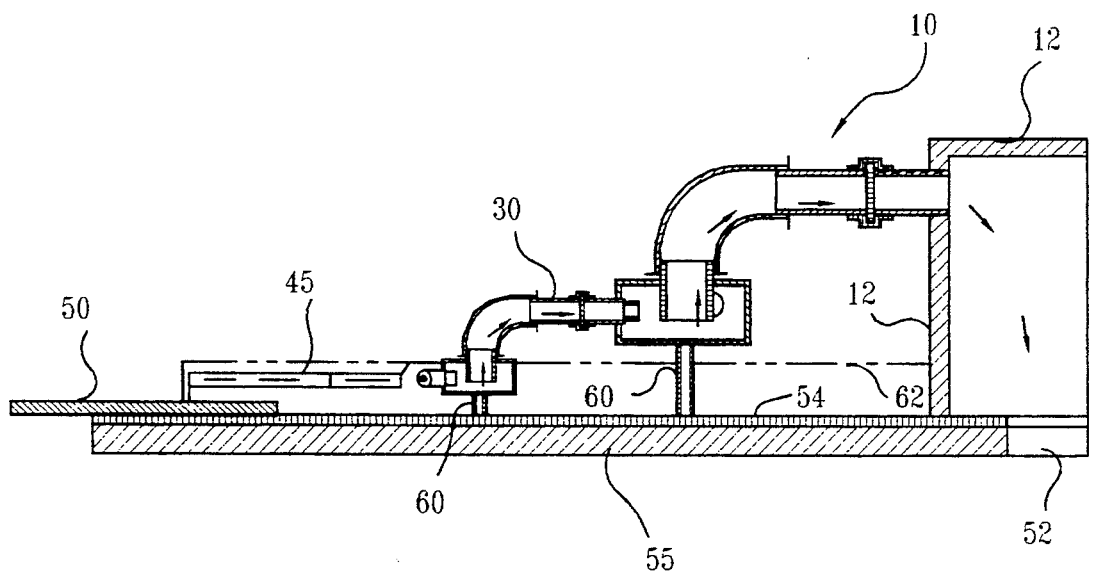
FIG. 2 is a view, in section, of apparatus similar to that of FIG. 1, installed as a collector.
Figure 3:
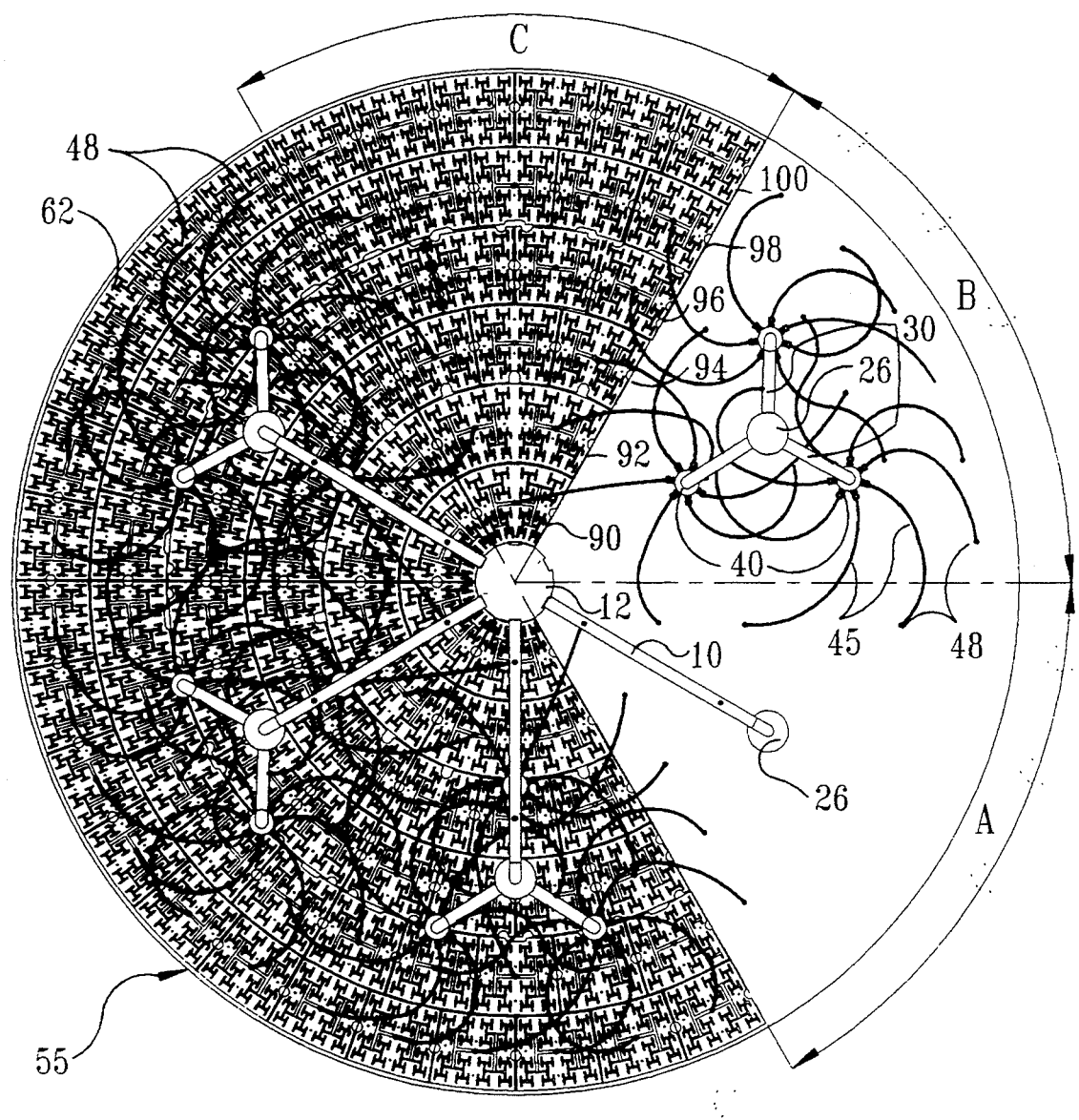
FIG. 3 is a plan view illustrating a typical layout of a manifold system of this invention, including three step-down stages to the step-down nozzles and three step-down stages within the step-down nozzles.

FIGS. 1 and 2 illustrate substantially similar structure constituting a single leg, designated generally 10, of a manifold system of the type illustrated more completely by FIG. 3. As shown by FIG. 1, a center well 12, which is a cylindrical plenum, receives liquid through a port 14. The liquid then flows as indicated by the arrows into the proximal end 15 of the primary conduit, designated generally 16, and including pipe lengths 17 and 18 and elbow 19, to discharge through the terminal end 20 into an intermediate plenum 26.

The system includes a plurality of primary conduits 16 extending at radially and equally spaced locations from the sidewall of the center well 12. In like fashion, a plurality of secondary conduits, indicated generally 30, and including pipe lengths 31 and 32 and elbow 33 provide fluid flow communication between the intermediate plenum 26 and a plurality of subsequent (as illustrated, terminal) plenums 40. The plurality of terminal plenums 40 corresponds in number to the plurality of secondary conduits 30 in the manifold system. Ideally, the respective flow paths from the center well to the individual outlets 41 of each terminal plenum 40 in the system are hydraulically equivalent so that the flow rate of liquid into the proximal ends 44 of tubing runs 45 is approximately identical.

Each of the plurality of runs 45 is approximately identical and each terminates in open flow communication with a recursive step-down nozzle 48. The step-down nozzles 48 are positioned in a pattern best shown by FIG. 3, with the individual tubing runs 45 taking whatever shape is required to accommodate the pattern. The nozzles 48 are not all of precisely the same shape, but are shown as nearly equal in size and shape as is practical in view of the constraints imposed by the circular cross section of the column.

FIG. 2 illustrates a manifold segment substantially the same as that illustrated by FIG. 1, but installed as a portion of a collector. That is, the step-down nozzles 50 are disposed in the vicinity of an outlet 52 and occupy an outlet zone 54 adjacent a structural plate 55. In both the distributor and collector arrangements illustrated by FIGS. 1 and 2, respectively, the manifold components are shown secured by structural elements 60 to a structural plate 55. For certain applications, a solid phase medium will fill the entire volume of a cell, commencing with a lower interface 62 at the top of the step-down nozzles 50 to an upper interface 63.

It will be understood that the number of intermediate plenums, terminal plenums, and step-down nozzles, as well as the placement, patterns and size of the step-down nozzles will be determined in substantial part by the diameter of the cell. The placement and arrangement of FIG. 3 is presently regarded as appropriate for a cell approximately 10 to 20 feet in diameter, in which fluid is delivered to an interface at approximately 200 to 1000 gallons per minute. The illustrated placement pattern effects a flow rate of approximately 0.025 to 0.125 gallons per minute through each orifice (8064 total orifices). Each step-down on the nozzle multiplies by four the number of outlet orifices. For example, one more step-down added to the nozzles of FIG. 3 results in 32,256 orifices and consequently, a closer approximation to ideal distribution. Additional nozzle step-down stages are particularly beneficial as the distributor diameter becomes very large (larger than 20 feet) or if it is desired to minimize differential velocity mixing at the orifice-fluid interface.

FIG. 3 illustrates a center well 12 supplying six primary conduits 10 (four of which are shown) which deliver liquid to six intermediate plenums 26 (best shown in segment A of FIG. 3). Each intermediate plenum 26 supplies three terminal plenums 40 through respective secondary conduits 30 (see segment B, FIG. 3). Each of the secondary plenums 40 delivers liquid through piping runs 45 to individual step-down nozzles 48 (see segment C, FIG. 3). Although the drawings illustrate most of the manifold system attached to the interior sides of the structural plates 55, it is within contemplation that all, or substantial portions of the conduits be external to the cell. Only the final orifices need be internal to the cell in practice.

Figure 4A:
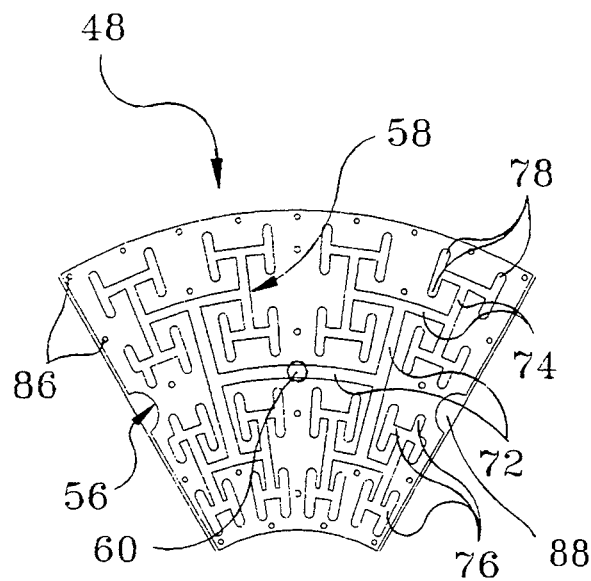
Figure 4B:
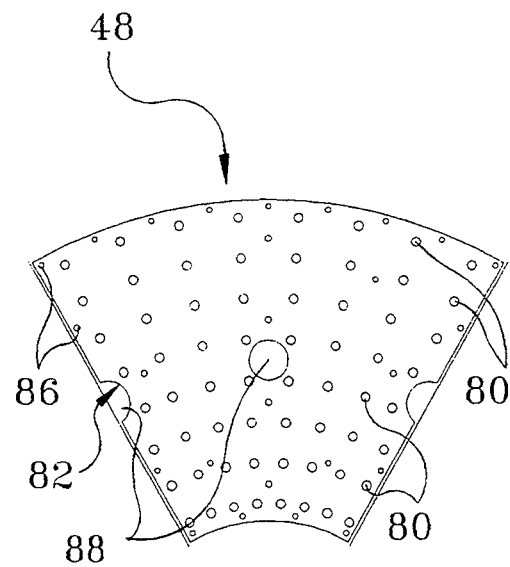
Figure 4C:
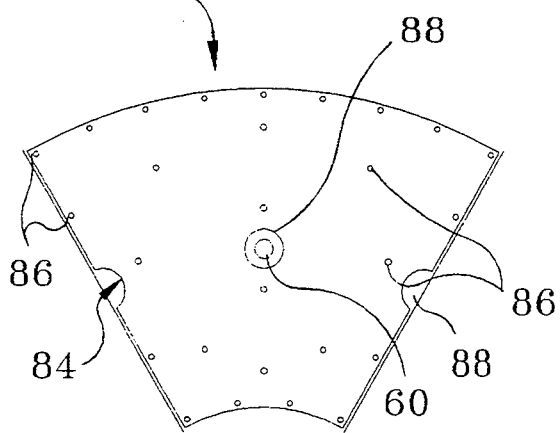

As best shown by FIG. 4, each step-down nozzle 48 includes a main plate 56 (FIG. 4a) which provides a fluid-distributing, milled flow channel, designated generally 58. The channel 58 receives fluid at an inlet 60 from a piping run 45 (FIG. 3). Fluid entering the nozzle 48 is distributed through a system of step-down stages 72, 74, 76, to a multiplicity of terminations 78. These terminations 78 register with outlet ports 80 through a nozzle exit plate 82 (FIG. 4b) which is fastened to the main plate 56 opposite the inlet 60. The sizing and arrangement of the channel stages 72, 74 and 76 are selected to deliver approximately equal flow through each of the ports 80. As shown by FIG. 4b, the arrangement of the respective ports 80 is approximately mutually equidistant from adjacent such ports 80. The nozzle assembly 48 is completed with a top plate 84 (FIG. 4c), the three plates 56, 82 and 84, being connected with fasteners (not shown) through bolt holes 86. A central opening 88 accommodates the inlet pipe 60. Large holes 89 through the plates 56, 82, 84 provide access to the support plate 55 (FIG. 3). The assembled nozzles may be anchored to the support plate 55 by suitable means, such as a washer (not shown) of larger diameter than the holes 89 held by a bolt (not shown) turned into a threaded hole (not shown) in the plate 55.

The recursive orifice pattern resulting from the use of more, or fewer, intermediate channel stages 74 and/or more, or fewer, terminal channel stages 76 allows for proper selection of a nozzle pattern and density that will insure optimum distribution of liquid passed through the flow path of the nozzle 48 to the cell in which the nozzle is placed. Similarly, nozzle density and placement can be optimized when a similar nozzle 50 is used as part of a collector system.

Generally the distributor and collector of this invention can be arranged to provide nearly identical hydraulic paths from an inlet well or outlet well 12 to each final orifice associated with that well. Good fluid distribution and hydraulic balance over a wide range of flow rates, e.g. a maximum flow rate as much as five times the minimum flow rate in a system, may be provided without the need for developing high pressure drops to force such distribution. In the preferred configurations, a substantially identical distance is traversed between a well 12, 14 and each final orifice 80.

An important aspect of the invention is the ability to maintain hydraulic balance and even flow distribution without sacrificing plug flow. While the invention is especially advantageous to large diameter cells, it can be applied to cells of any size.

For cells having a circular cross section, a preferred nozzle pattern is as shown in FIG. 3. As shown, the nozzles 48 are generally fan shaped and are placed in concentric rings around the well 12. A first ring 90 is formed by nozzles 48 placed side-by-side around the well 12. Each subsequent ring 92, 94, 96, 98, and 100 of nozzles 48 is also formed by placing nozzles in side-by-side relationship. The nozzles 48 are packed in the rings in abutment with adjacent nozzles of the same and adjacent rings. The nozzle dimensions are selected so that the number of nozzles in each ring, 94–100, outside the innermost ring 92 is equal to the number of the ring away from the cell 12, multiplied by the number of nozzles in the first ring. As shown, six nozzles 48 are contained within the innermost ring 92, twelve in the next ring 94 and thirty six in the sixth, or outermost ring 100.

Reference herein to the details of the illustrated embodiments is not intended to restrict the scope of the appended claims which themselves recite those details regarded as important to the invention.

What is claimed is:

1. A uniform fluid distributor for use with a liquid transfer manifold system for maintaining an interface between liquid phases within a large scale separator system including a cell of circular cross-section into which liquid is introduced as discrete phases at an inlet zone occupying a first approximately transverse cross-sectional region of said cell whereby to develop a discrete liquid phase plug which migrates approximately longitudinally in a direction normal said first cross-sectional region towards an outlet zone occupying a second approximately transverse cross-sectional region of said cell, said manifold system including a center well, positioned approximately at the center of one of said transverse cross-sectional regions and a plurality of approximately hydraulically identical recursive step-down fluid distribution conduit systems, each including a plurality of terminal discharge ends; wherein said uniform fluid distributor, comprises:

a plurality of fan-shaped step-down nozzles connected to respective said discharge ends, a flow path in each said step-down nozzle including a fluid flow channel constructed and arranged to receive fluid flow from a said discharge end, and a plurality of orifices through which liquid entering said step-down nozzle is distributed to said cell, said orifices being arranged in a recursive pattern with respect to said flow channel whereby each orifice discharges an approximately equal portion of fluid received from said terminal end and wherein said step-down nozzles are arranged substantially engaging, side-by-side relationship in adjacent successive rings encircling said center well.

2. A uniform fluid distributor as in claim 1, wherein said successive rings include a first ring of fan shaped step-down nozzles in a side-by-side substantially engaging relationship and additional concentric rings of fan shaped step-down nozzles in a side-by-side substantially engaging relationship and with the step-down nozzles of each ring in a substantially engaging, packed arrangement with the step-down nozzles of the adjacent inward ring.

3. A uniform fluid distributor as in claim 2 wherein each additional concentric ring includes a number of step-down nozzles equal to the number of step-down nozzles in the first ring times the number of the ring, counted from the well.

4. A uniform fluid distributor for use with a liquid transfer manifold system in a cell of a large scale separator system into which liquid is introduced as discrete phases at an inlet zone occupying a first approximately transverse cross-sectional region of said cell whereby to develop a discrete liquid phase plug which migrates approximately longitudinally in a direction normal said first cross-sectional region towards an outlet zone occupying a second approximately transverse cross-sectional region of said cell, and a central well comprising:

a step-down nozzle at the terminal end of said manifold system, said step-down nozzle being structured and arranged with flow channels interconnected in a recursive manner in fluid flow relationship with a plurality of orifices through which liquid entering said step-down nozzle is distributed to said cell along an approximately horizontal plane, said orifices being arranged in an approximately equally spaced pattern, and said step down nozzles being arranged side-by-side in concentric rings encircling said center well, with adjacent step-down nozzles of each said ring being in substantially engaging relationship.

5. A uniform fluid distributor as in claim 4, wherein said concentric rings include an inner ring of fan shaped step-down nozzles in side-by-side relationship and additional outer rings of fan shaped step-down nozzles in substantially side-by-side relationship, and with the step-down nozzles of each ring substantially engaging step-down nozzles of adjacent rings.

6. A uniform fluid distributor as in claim 5 wherein each said additional concentric ring includes a number of step-down nozzles equal to the number of step-down nozzles in the inner ring times the number of said additional outer ring counted from the well.

7. A uniform fluid distributor for use with a liquid transfer manifold system for maintaining an interface between liquid phases within a large scale separator system including a cell into which liquid is introduced as discrete phases at an inlet zone occupying a first approximately transverse cross-sectional region of said cell whereby to develop a discrete liquid phase plug which migrates approximately longitudinally in a direction normal said first cross-sectional region towards an outlet zone occupying a second approximately transverse cross-sectional region of said cell, said manifold system including a center well, positioned approximately at the center of one of said transverse cross-sectional regions and a plurality of approximately hydraulically identical recursive step-down fluid distribution conduit systems, each including a plurality of terminal discharge ends; wherein said uniform fluid distributor, comprises:

a plurality of step-down nozzles connected to respective said discharge ends, a flow path in each said step-down nozzle including a fluid flow channel constructed and arranged to receive fluid flow from a said discharge end, and a plurality of orifices through which liquid entering said step-down nozzle is distributed to said cell, said orifices being arranged in a recursive pattern with respect to said flow channel whereby each orifice discharges an approximately equal portion of fluid received from said terminal end.

* * * * *